(12) United States Patent
Mavunkel et al.

(10) Patent No.: US 7,214,679 B2
(45) Date of Patent: May 8, 2007

(54) PIPERIDINE/PIPERAZINE-TYPE INHIBITORS OF P38 KINASE

(75) Inventors: Babu J. Mavunkel, Sunnyvale, CA (US); Sundeep Dugar, San Jose, CA (US); Gregory R. Luedtke, Morgan Hill, CA (US); Xuefei Tan, Sunnyvale, CA (US); Glen McEnroe, San Mateo, CA (US)

(73) Assignee: Scios, Inc., Mountain View, CA (US)

( * ) Notice: Subject to any disclaimer, the term of this patent is extended or adjusted under 35 U.S.C. 154(b) by 0 days.

(21) Appl. No.: 10/757,023

(22) Filed: Jan. 13, 2004

(65) Prior Publication Data

US 2004/0176382 A1 Sep. 9, 2004

Related U.S. Application Data

(62) Division of application No. 09/990,184, filed on Nov. 20, 2001, now Pat. No. 6,696,443.

(60) Provisional application No. 60/252,196, filed on Nov. 20, 2000.

(51) Int. Cl.
*C07D 295/03* (2006.01)
*C07D 403/12* (2006.01)
*C07D 403/14* (2006.01)
*A61K 31/496* (2006.01)

(52) U.S. Cl. .......... 514/253.01; 544/360; 544/363; 544/364; 544/368; 544/369; 544/370; 544/376; 544/379; 544/371; 544/372; 544/391; 514/253.05; 514/253.06; 514/253.1; 514/253.09; 514/253.11; 514/254.04; 514/254.02; 514/254.05

(58) Field of Classification Search .......... 544/360, 544/363, 364, 368, 369, 370, 376, 379, 371, 544/372, 391; 514/253.05, 253.06, 253.01, 514/253.1, 253.09, 253.11, 254.04, 254.02, 514/254.05, 255.01
See application file for complete search history.

(56) References Cited

U.S. PATENT DOCUMENTS

| 5,340,809 A | * | 8/1994 | Gaudry et al. | ......... | 514/254.05 |
| 6,130,235 A | | 10/2000 | Mavunkel et al. | .......... | 514/322 |

FOREIGN PATENT DOCUMENTS

| EP | 0 512 352 | 11/1992 |
| WO | WO 96/40143 | 12/1996 |
| WO | WO 97/26252 | 7/1997 |
| WO | WO 98/06715 | 2/1998 |
| WO | WO 98/07425 | 2/1998 |
| WO | WO 99/31096 | 6/1999 |
| WO | WO 99/61426 | 12/1999 |
| WO | WO 00/12074 | 3/2000 |
| WO | WO 00/59904 | 10/2000 |
| WO | WO 00/71535 | 11/2000 |

OTHER PUBLICATIONS

Scott et al. (1995). *Journal of Medicinal Chemistry* 38(21):4198-4210.
Chalmers (1996). *TIPS* 17:166-172.

* cited by examiner

*Primary Examiner*—Kahsay Habte
(74) *Attorney, Agent, or Firm*—Morrison & Foerster LLP

(57) ABSTRACT

Compounds of the formula:

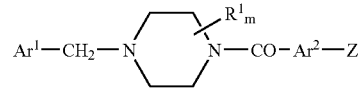

wherein the substituents are as defined herein are useful for treating conditions mediated by p38 kinase.

20 Claims, No Drawings

PIPERIDINE/PIPERAZINE-TYPE INHIBITORS OF P38 KINASE

CROSS-REFERENCE TO RELATED APPLICATIONS

This application is a divisional of U.S. Ser. No. 09/990,184 filed 20 Nov. 2001 now U.S. Pat. No. 6,696,443 and now allowed which claims priority under 35 U.S.C. § 119(e) from provisional application U.S. Ser. No. 60/252,196 filed 20 Nov. 2000. The contents of these documents are incorporated herein by reference.

FIELD OF THE INVENTION

The invention relates to treating various disorders associated with enhanced activity of kinase p38-α. More specifically, it concerns piperadine and piperazine derivatives useful in these methods.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

Eye diseases associated with a fibroproliferative condition include retinal reattachment surgery accompanying proliferative vitreoretinopathy, cataract extraction with intraocular lens implantation, and post glaucoma drainage surgery.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3-or 4-position with a piperazine ring linked through a carboxamide linkage. Additional compounds which are conjugates of pipera zines with indoles are described as insecticides in WO97/26252, also incorporated herein by reference.

Certain aroyl/phenyl-substituted piperazines and piperidines which inhibit p38-α kinase are described in PCT publication WO00/12074 published 9 Mar. 2000. In addition, indolyl substituted piperidines and piperazines which inhibit this enzyme are described in PCT publication No. WO99/61426 published 2 Dec. 1999. Carbolene derivatives of piperidine and piperazine as p38-α inhibitors are described in PCT/US00/07934 filed 24 Mar. 2000.

None of the foregoing patents describes the piperadine type derivatives described herein which specifically inhibit p38-α.

SUMMARY OF THE INVENTION

The invention is directed to methods and compounds useful in treating conditions that are characterized by enhanced p38-α activity. These conditions include inflammation, proliferative diseases, and certain cardiovascular disorders as well as Alzheimer's disease as further described below.

Compounds of the invention inhibit p38 kinase, the α-isoform in particular, and are thus useful in treating diseases mediated by these activities. The compounds of the invention are of the formula (1):

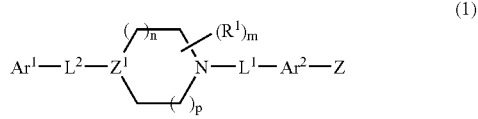

(1)

and the pharmaceutically acceptable salts thereof, or a pharmaceutical composition thereof, wherein:

$Ar^1$ is an aryl group substituted with 0–5 non-interfering substituents, wherein two adjacent noninterfering substituents can form a fused aromatic or nonaromatic ring;

$L^1$ and $L^2$ are linkers;

each $R^1$ is independently a noninterfering substituent;

$Z^1$ is $CR^2$ or N wherein $R^2$ is hydrogen or a noninterfering substituent;

m is 0–4;

each of n and p is an integer from 0–2 wherein the sum of n and p is 0–3;

$Ar^2$ is a substantially planar, monocyclic or polycyclic aromatic moiety having one or more optional ring heteroatoms, said moiety being optionally substituted with one or more non-interfering substituents, two or more of which may form a fused ring;

Z is $-W_i-COX_jY$ wherein Y is $COR^3$ or an isostere thereof; $R^3$ is a noninterfering substituent, each of W and X is a spacer of 2–6 Å, and each of i and j is independently 0 or 1;

wherein the smallest number of covalent bonds in the compound separating the atom of $Ar^1$ bonded to $L^2$ to the atom of $Ar^2$ bonded to $L^1$ is at least 6, where each of said bonds has a bond length of 1.2 to 2.0 angstroms; and/or wherein the distance in space between the atom of $Ar^1$ bonded to $L^2$ and the atom of $Ar^2$ bonded to $L^1$ is 4.5–24 angstroms;

with the proviso that the portion of the compound represented by $Ar^2$—Z is not

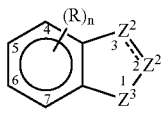

wherein ↷ represents a single or double bond; n is 0–3; one $Z^2$ is CA or CRA and the other is CR, $CR_2$, NR or N; A is —$W_i$—$COX_jY$ wherein Y is COR or an isostere thereof, each of W and X is a spacer of 2–6Å, and each of i and j is independently 0 or 1; $Z^3$ is NR or O; and each R is independently hydrogen or a noninterfering substituent.

The invention is further directed to methods of treating inflammation or proliferative conditions using these compounds. The invention is also directed to treating conditions associated with cardiac failure and Alzheimer's disease using the invention compounds.

DETAILED DESCRIPTION

The compounds of formula (1) are useful in treating conditions which are characterized by overactivity of p38 kinase, in particular the α-isoform. Conditions "characterized by enhanced p38-α activity" include those where this enzyme is present in increased amount or wherein the enzyme has been modified to increase its inherent activity, or both. Thus, "enhanced activity" refers to any condition wherein the effectiveness of these proteins is undesirably high, regardless of the cause.

The compounds of the invention are useful in conditions where p38-α kinase shows enhanced activity. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states, spinal chord injury and traumatic or surgical wounds. These conditions, of course, would be benefited by compounds which inhibit p38-α. Methods of treatment with the compounds of the invention are further discussed below.

The compounds useful in the invention are derivatives of piperadine/piperazine-type compounds containing a mandatory substituent, Z attached to the aromatic moiety $Ar^2$. The aromatic moiety is a substantially planar, monocyclic or polycyclic aromatic moiety having one or more optional ring heteroatoms. The aromatic moiety may be optionally substituted with one or more non-interfering substituents, two or more of which may form a fused ring.

In somewhat greater detail the aromatic moiety $Ar^2$ comprises an optionally substituted monocyclic or polycyclic aromatic nucleus, wherein the aromatic nucleus consists of a carbocyclic or heterocyclic ring selected from (i) a five-membered heterocyclic or carbocyclic ring (ii) a six-membered carbocyclic or heterocyclic ring; (iii) a five-membered carbocyclic or heterocyclic ring fused to another five-membered carbocyclic or heterocyclic ring; (iv) a six-membered carbocyclic or heterocyclic ring fused to another six-membered carbocyclic or heterocyclic ring; and (v) a five-membered heterocyclic or carbocyclic ring fused to a six-membered carbocyclic or heterocyclic ring. Examples of the foregoing include the following aromatic moieties:

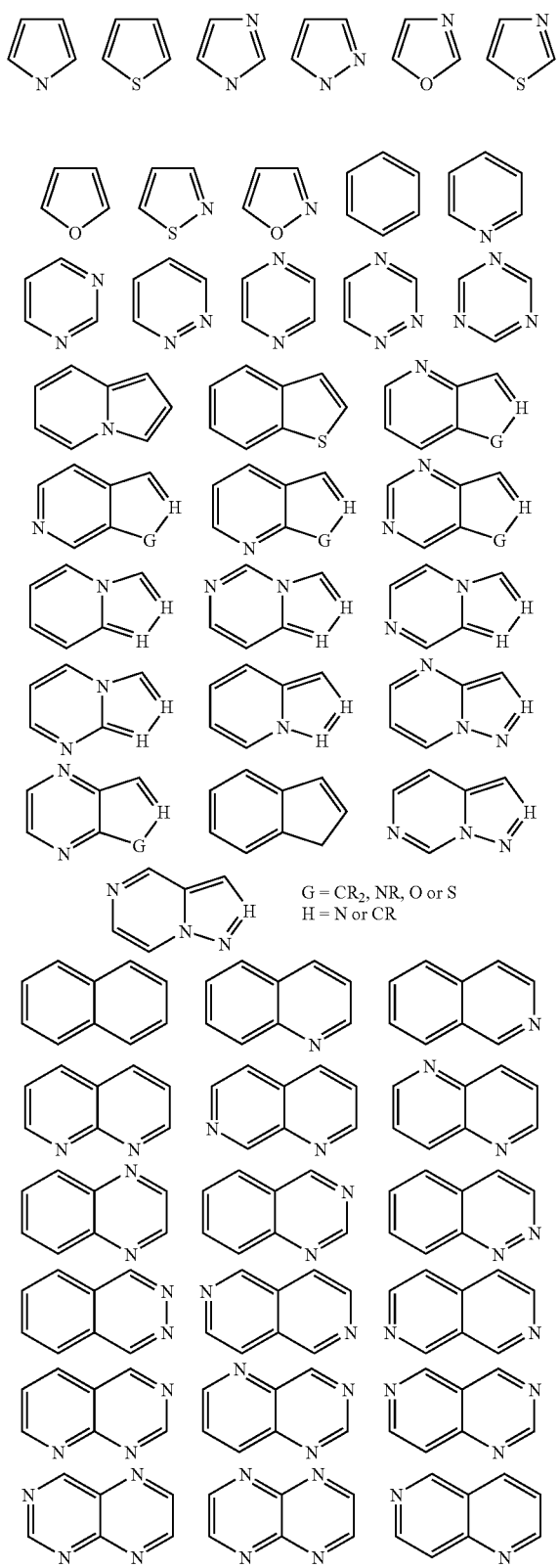

-continued

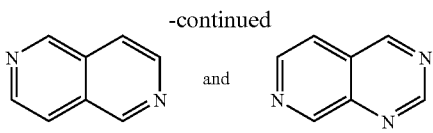

where R is a noninterfering substituent.

Particular examples of $Ar^2$ in formula (1) are such that the portion of compound (1) represented by $L^1$—$Ar^2$—Z is selected from the following:

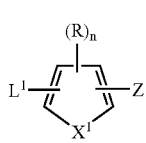

(I)

wherein n is 0, 1 or 2; $X^1$ is NR, $CR_2$, O or S; and each R is independently H or a noninterfering substituent; and two or more R groups may form a fused ring;

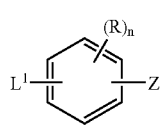

(II)

wherein n is 0–4; R is H or a noninterfering substituent where two or more R groups may form a fused ring; and one or more ring carbons may be optionally replaced with nitrogen;

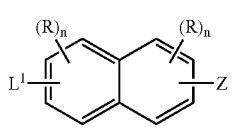

(III)

wherein each n is independently 0 to 3; R is H or a noninterfering substituent, where two or more R groups may form a fused ring; and one or more ring carbons may be optionally replaced with nitrogen;

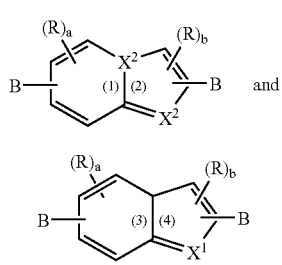

(IV-a)

(IV-b)

wherein, subject to the proviso set forth above with respect to formula (1), one B is $L^1$ and the other is Z; wherein a is 0 to 4 such that the positions on the six membered rings (1) and (3) to which $(R)_a$ is bonded can include $X^2$ when $X^2$ is C; b is 0–3 such that the positions on the five-membered rings (2) and (4) to which $(R)_b$ is bonded can include $X^2$ and $X^1$, when $X^2$ is C and $X^1$ is N or C; each $X^2$ is independently N or CR; $X^1$ is NR, $CR_2$, O or S; each R is H or a noninterfering substituent where two or more R groups may form a fused ring; wherein one or more of the ring carbons that are at positions other than $X^2$ or $X^1$ and that are also not bound to B can be optionally replaced with N;

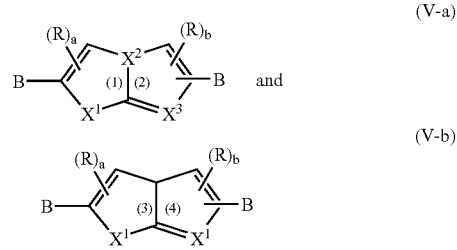

(V-a)

(V-b)

wherein one B is $L^1$ and the other is Z; a is 0–4 such that the positions on the rings (1) and (3) to which $(R)_a$ can be bonded include $X^2$ and $X^1$ where $X^2$ is C and $X^1$ is C or N; b is 0 or 3 such that the positions on the rings (2) and (4) to which $(R)_b$ can be bonded include $X^1$, $X^2$ and $X^3$ when $X^1$ is C or N and $X^2$ and/or $X^3$ are C; each $X^1$ is independently NR, $C(R)_2$, O or S; $X^2$ and $X^3$ are independently N or CR; each R is independently H or a noninterfering substituent where two or more R groups can optionally form a fused ring; wherein one or more of the ring carbons that are at positions other than $X^1$, $X^2$ or $X^3$, and that are also not bound to B, can be optionally replaced with N.

Certain positions of the molecule of formula I are described as permitting "noninterfering substituents." This terminology is used because the substituents in these positions generally speaking are not relevant to the essential activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound of formula (1) to inhibit p38-α activity qualitatively intact. Thus, the substituent may alter the degree of inhibition of p38-α. However, as long as the compound of formula (1) retains the ability to inhibit p38-α activity, the substituent will be classified as "noninterfering." A number of assays for determining the ability of any compound to inhibit p38-α activity are available in the art. A whole blood assay for this evaluation is illustrated below. The gene for p38-α has been cloned and the protein can be prepared recombinantly and its activity assessed, including an assessment of the ability of an arbitrarily chosen compound to interfere with this activity. The essential features of the molecule are tightly defined. The positions which are occupied by "noninterfering substituents" can be substituted by conventional organic moieties as is understood in the art. It is irrelevant to the present invention to test the outer limits of such substitutions. The essential features of the compounds are those set forth with particularity herein.

In addition, $L^1$ and $L^2$ are described herein as linkers. The nature of such linkers is less important than the distance they impart between the portions of the molecule. Typical linkers include alkylene, i.e. $(CH_2)_n$—R; alkenylene—i.e., an alkylene moiety which contains a double bond, including a double bond at one terminus. Other suitable linkers include, for example, substituted alkylenes or alkenylenes, carbonyl moieties, and the like.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or contain heteroatoms within the "backbone" of the hydrocarbyl residue.

As used herein, "inorganic residue" refers to a residue that does not contain carbon. Examples include, but are not limited to, halo, hydroxy, $NO_2$, or $NH_2$.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1–10C (alkyl) or 2–10C (alkenyl or alkynyl). Preferably they contain 1–6C (alkyl) or 2–6C (alkenyl or alkynyl). Heteroalkyl, heteroalkenyl and heteroalkynyl are similarly defined but may contain 1–2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

The term "Aromatic" with respect to moiety $Ar^1$ refers to a monocyclic or fused bicyclic moiety such as phenyl or naphthyl; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroalkyl" refer to aromatic and heteroaromatic systems which are coupled to another residue through a carbon chain, including substituted or unsubstituted, saturated or unsaturated, carbon chains, typically of 1–6C. These carbon chains may also include a carbonyl group, thus making them able to provide substituents as an acyl moiety.

When the compounds of Formula (1) contain one or more chiral centers, the invention includes optically pure forms as well as mixtures of stereoisomers or enantiomers With respect to the portion of the compound between the $Ar^1$ and $Ar^2$, linkers $L^2$ and $L^1$, in combination with the piperadine/piperazine ring, provide for separation of the atom of $Ar^1$ bonded to $L^2$ from the atom of $Ar^2$ bonded to $L^1$ by a defined minimum number of covalent bond lengths counted end-to-end through the compound, as opposed to a measurement of linear distance through space. More particularly, the smallest number of bonds counted end-to-end in the compound separating the atom of $Ar^1$ bonded to $L^2$ from the atom of $Ar^2$ bonded to $L^1$ is at least 5, and preferably from 6 to 12, wherein the length of each of such bonds is 1.2 to 2.0 angstroms. In terms of a linear distance through space, the linear distance measured through space from the atom of $Ar^1$ bonded to $L^2$ to the atom of $Ar^2$ bonded to $L^1$ is a distance of 4.5–24Å, preferably 6–20Å, and more preferably 7.5–10Å.

Typical, but nonlimiting, embodiments of $L^1$ and $L^2$ are CO and isosteres thereof, or optionally substituted isosteres, or longer chain forms. $L^2$, in particular, may be alkylene or alkenylene optionally substituted with noninterfering substituents or $L^1$ or L2 may be or may include a heteroatom such as N, S or O. Such substituents include, but are limited to, a moiety selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two substituents on $L^2$ can be joined to form a non-aromatic saturated or unsaturated ring that includes 0–3 heteroatoms which are O, S and/or N and which contains 3 to 8 members or said two substituents can be joined to form a carbonyl moiety or an oxime, oximeether, oximeester or ketal of said carbonyl moiety.

Isosteres of CO and $CH_2$, include SO, $SO_2$, or CHOH. CO and $CH_2$ are preferred. Thus, $L^2$ is substituted with 0–2 substituents. Where appropriate, two optional substituents on $L^2$ can be joined to form a non-aromatic saturated or unsaturated hydrocarbyl ring that includes 0–3 heteroatoms such as O, S and/or N and which contains 3 to 8 members. Two optional substituents on $L^2$ can be joined to form a carbonyl moiety which can be subsequently converted to an oxime, an oximeether, an oximeester, or a ketal.

$Ar^1$ is aryl, heteroaryl, including 6–5 fused heteroaryl, cycloaliphatic or cycloheteroaliphatic that can be optionally substituted. Ar is preferably optionally substituted phenyl.

Each substituent on $Ar^1$ is independently a hydrocarbyl residue (1–20C) containing 0–5 heteroatoms selected from O, S and N, or is an inorganic residue. Preferred substituents include those selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3–8 members. More preferred substituents include halo, alkyl (1–4C) and more preferably, fluoro, chloro and methyl. These substituents may occupy all available positions of the aryl ring of $Ar^1$, preferably 1–2 positions, most preferably one position. These substituents may be optionally substituted with substituents similar to those listed. Of course some substituents, such as halo, are not further substituted, as known to one skilled in the art.

Two substituents on $Ar^1$ can be joined to form a fused, optionally substituted aromatic or nonaromatic, saturated or unsaturated ring which contains 3–8 members.

Between $L^1$ and $L^2$ is a piperidine-type moiety of the following formula:

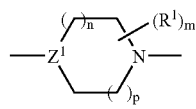

wherein $Z^1$ is $CR^2$ or N and $R^2$ is H or a noninterfering substituent. Each of n and p is an integer from 0–2 wherein the sum of n and p is 0–3. The noninterfering substituents $R^2$ include, without limitation, halo, alkyl, alkoxy, aryl, arylalkyl, aryloxy, heteroaryl, acyl, carboxy, or hydroxy. Preferably, $R^2$ is H, alkyl, OR, $NR_2$, SR or halo, where R is H or alkyl. Additionally, $R^2$ can be joined with an $R^1$ substituent to form an optionally substituted non-aromatic saturated or unsaturated hydrocarbyl ring which contains 3–8 members and 0–3 heteroatoms such as O, N and/or S. Preferred embodiments include compounds wherein $Z^1$ is CH or N, and those wherein both n and p are 1.

$R^1$ represents a noninterfering substituent such as a hydrocarbyl residue (1–20C) containing 0–5 heteroatoms selected from O, S and N. Preferably $R^1$ is alkyl, alkoxy, aryl, arylalkyl, aryloxy, heteroalkyl, heteroaryl, heteroarylalkyl, RCO, =O, acyl, halo, CN, OR, NRCOR, NR, wherein R is H, alkyl (preferably 1–4C), aryl, or hetero forms thereof. Each appropriate substituent is itself unsubstituted or substituted with 1–3 substituents. The substituents are preferably independently selected from a group that includes alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^1$ on adjacent positions can be joined to form a fused, optionally substituted aromatic or nonaromatic, saturated or unsaturated ring which contains 3–8 members, or $R^1$ is =O or an oxime, oximeether, oximeester or ketal thereof. $R^1$ may occur m times on the ring; m is an integer of 0–4. Preferred embodiments of $R^1$ comprise alkyl (1–4C) especially two alkyl substituents and carbonyl. Most preferably $R^1$ comprises two methyl groups at positions 2 and 5 or 3 and 6 of a piperidinyl or piperazinyl ring or =O preferably at the 5-position of the ring. The substituted forms may be chiral and an isolated enantiomer may be preferred.

Z is —$W_i$—$COX_jY$ wherein Y is $COR^3$ or an isostere thereof and $R^3$ is a noninterfering substituent. Each of W and X is a spacer and may be, for example, optionally substituted alkyl, alkenyl, or alkynyl, each of i and j is 0 or 1. Preferably, W and X are unsubstituted. Preferably, j is 0 so that the two carbonyl groups are adjacent to each other. Preferably, also, i is 0 so that the proximal CO is adjacent the ring. However, compounds wherein the proximal CO is spaced from the ring can readily be prepared by selective reduction of an initially glyoxal substituted $Ar^2$.

The noninterfering substituent represented by $R^3$, when $R^3$ is other than H, is a hydrocarbyl residue (1–20C) containing 0–5 heteroatoms selected from O, S and/or N or is an inorganic residue. Preferred are embodiments wherein $R^3$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, SR, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl or aryl or the heteroatom-containing forms thereof, or wherein $R^3$ is OR, $NR_2$, SR, $NRCONR_2$, $OCONR_2$, or $NRSO_2NR_2$, wherein each R is independently H, alkyl, alkenyl or aryl or the heteroatom-containing forms thereof, and wherein two R attached to the same atom may form a 3–8 member ring and wherein said ring may further be substituted by alkyl, alkenyl, alkynyl, aryl, arylalkyl, heteroalkyl, heteroaryl, heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl or aryl or the heteroatom-containing forms thereof wherein two R attached to the same atom may form a 3–8 member ring, optionally substituted as above defined.

Other preferred embodiments of $R^3$ are H, heteroarylalkyl, —$NR_2$, heteroaryl, —COOR, —$NHRNR_2$, heteroaryl-COOR, heteroaryloxy, —OR, heteroaryl-$NR_2$, —NROR and alkyl. Most preferably $R^3$ is isopropyl piperazinyl, methyl piperazinyl, dimethylamine, piperazinyl, isobutyl carboxylate, oxycarbonylethyl, morpholinyl, aminoethyldimethylamine, isobutyl carboxylate piperazinyl, oxypiperazinyl, ethylcarboxylate piperazinyl, methoxy, ethoxy, hydroxy, methyl, amine, aminoethyl pyrrolidinyl, aminopropanediol, piperidinyl, pyrrolidinyl-piperidinyl, or methyl piperidinyl.

Isosteres of $COR^3$ as represented by Y are defined as follows. The isosteres have varying lipophilicity and may contribute to enhanced metabolic stability. Thus, Y, as shown, may be replaced by the isosteres in Table 1.

TABLE 1

Acid Isosteres

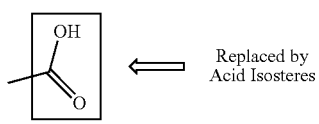

| Names of Groups | Chemical Structures | Substitution Groups (SG) |
|---|---|---|
| tetrazole | ![tetrazole] | n/a |
| 1,2,3-triazole | ![1,2,3-triazole with SG] | H; $SCH_3$; $COCH_3$; Br; $SOCH_3$; $SO_2CH_3$; $NO_2$; $CF_3$; CN; COOMe |
| 1,2,4-triazole | ![1,2,4-triazole with SG] | H; $SCH_3$; $COCH_3$; Br; $SOCH_3$; $SO_2CH_3$; $NO_2$ |

TABLE 1-continued

Acid Isosteres

| | | |
|---|---|---|
| | ⇐ | Replaced by Acid Isosteres |
| imidazole | | H; SCH₃; COCH₃; Br; SOCH₃; SO₂CH₃; NO₂ |

Thus, isosteres include tetrazole, 1,2,3-triazole, 1,2,4-triazole and imidazole.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

Copending, commonly-assigned U.S. Ser. No. 09/575,060, incorporated herein by reference in its entirety, illustrated the following reaction scheme for conversion of a 4-benzyl piperidinyl-indole-5-carboxamide to the glyoxalic acid compounds of the invention and derivatives thereof:

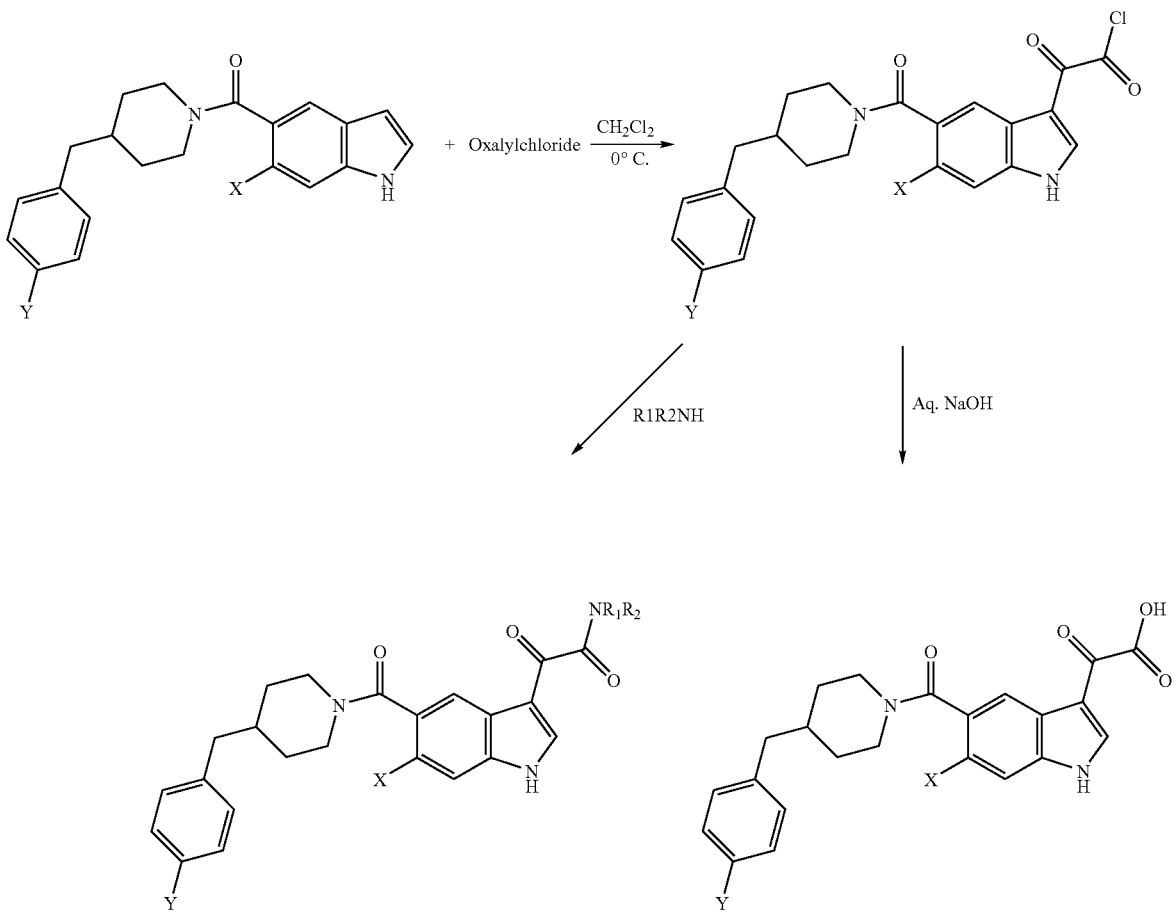

X = OCH₃, Cl, CH₃; Y = H, Halogen etc.
NR₁R₂ = NH₂, NH-Alkyl, NH-Aryl, N-Dialkyl, etc In the present invention, the indole moiety is generalized to Ar² in formula (1) above where Ar² is a substantially planar, monocyclic or polycyclic aromatic moiety having one or more optional ring heteroatoms, said moiety being optionally substituted with one or more non-interfering substituents, two or more of which may form a fused ring. Preferably the moiety Ar² comprises an optionally substituted monocyclic or polycyclic aromatic nucleus, wherein said aromatic nucleus consists of carbocyclic or heterocyclic ring selected from (i) a five-membered heterocyclic or carbocyclic ring (ii) a six-membered carbocyclic or heterocyclic ring; (iii) a five-membered carbocyclic or heterocycloc ring fused to another five-membered carbocyclic or heterocyclic ring; (iv) a six-membered carbocyclic or heterocyclic ring fused to another six-membered carbocyclic or heterocyclic ring; and (v) a five-membered heterocyclic or carbocyclic ring fused to a six-membered carbocyclic or heterocyclic ring. Formula (1), as required by the proviso stated above, excludes the indole type compounds disclosed and claimed in U.S. Ser. No. 09/575,060 filed May 21, 1999 and incorporated herein by reference.

As disclosed commonly assigned in U.S. Ser. No. 09/575,060, the glyoxal type substituent at position 3 can be generalized to —W$_i$COX$_j$Y.

The Ar² moiety may be generalized as:

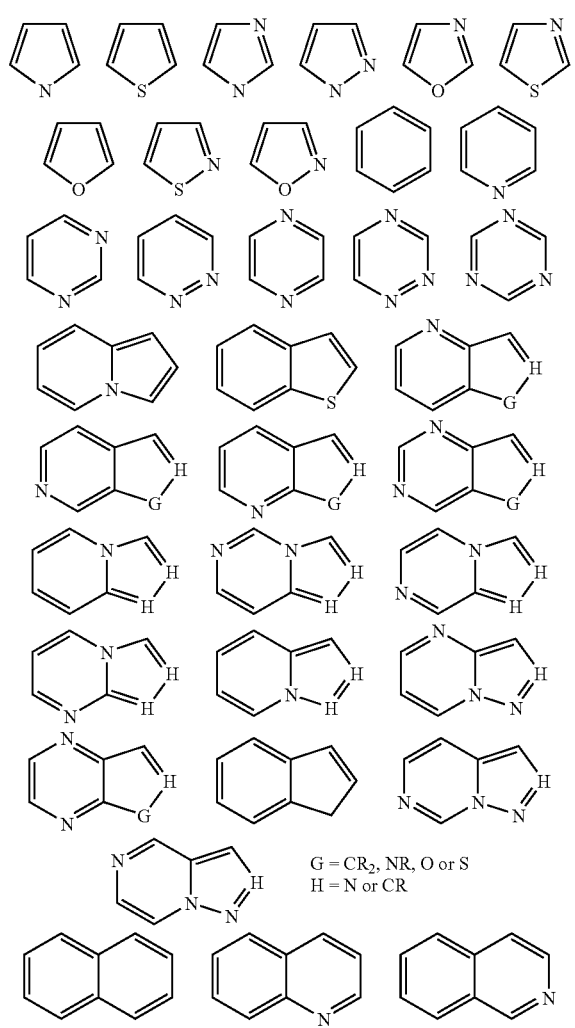

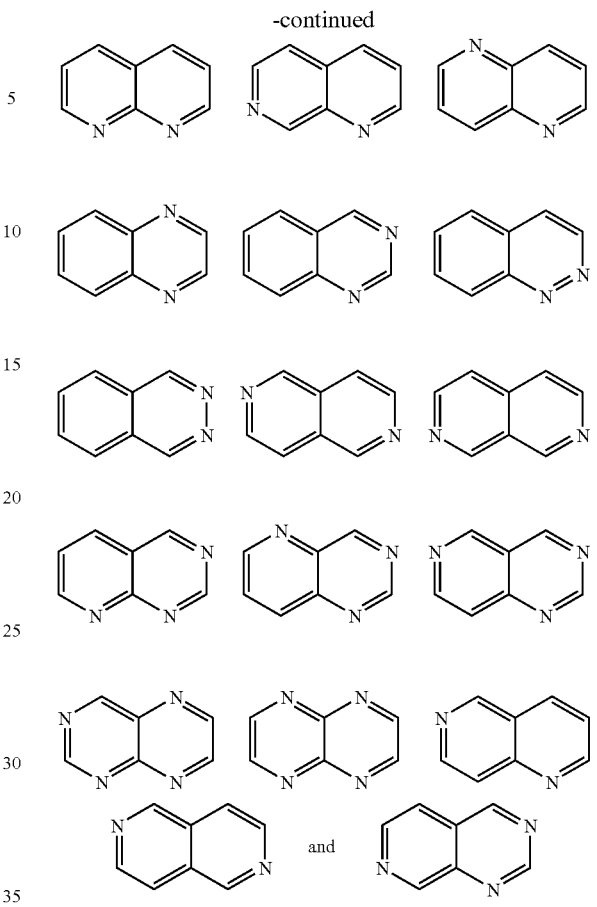

Methods to synthesize the compounds of the invention are, in general, known in the art. For example, commonly assigned U.S. Ser. No. 09/575,060, incorporated herein by reference in its entirety, disclosed that piperidine moieties can be obtained using the following reaction scheme

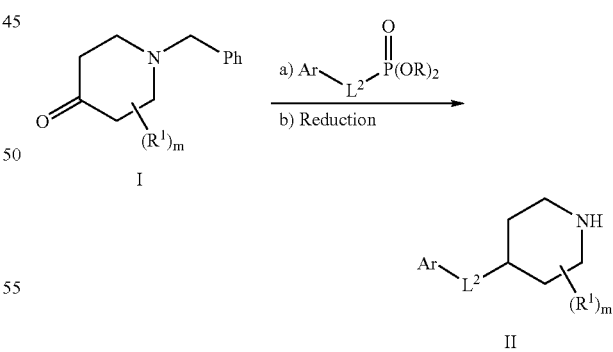

where an appropriate piperidone such as I, is treated with substituted benzyl phosphonate esters in the presence of a base such as sodium hydride to give alkenes which can be reduced to the corresponding substituted 4-benzylpiperidine such as II. The hydrogenations are typically done in the presence of catalytic metals in solvents such as methanol, ethanol and ethyl acetate.

An alternative to the above disclosed in U.S. Ser. No. 09/575,060 as follows:

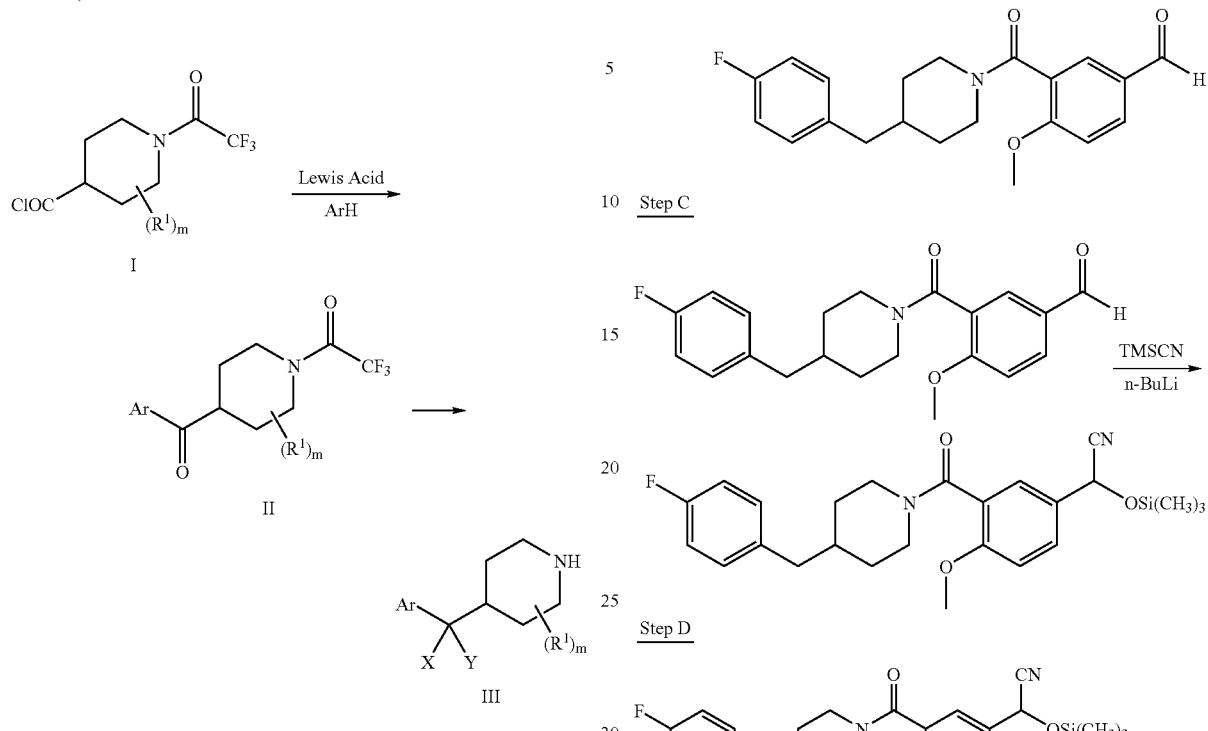

where isonipecotoyl chlorides such as I can be used to acylate appropriately substituted benzenes (ArH) in the presence of a Lewis acid such as aluminum chloride to give the ketones II. Further modifications of the carbonyl moiety of II using methods and routes generally known can then lead to the desired compounds III.

The following reaction schemes illustrate methods for preparing compounds of the present invention.

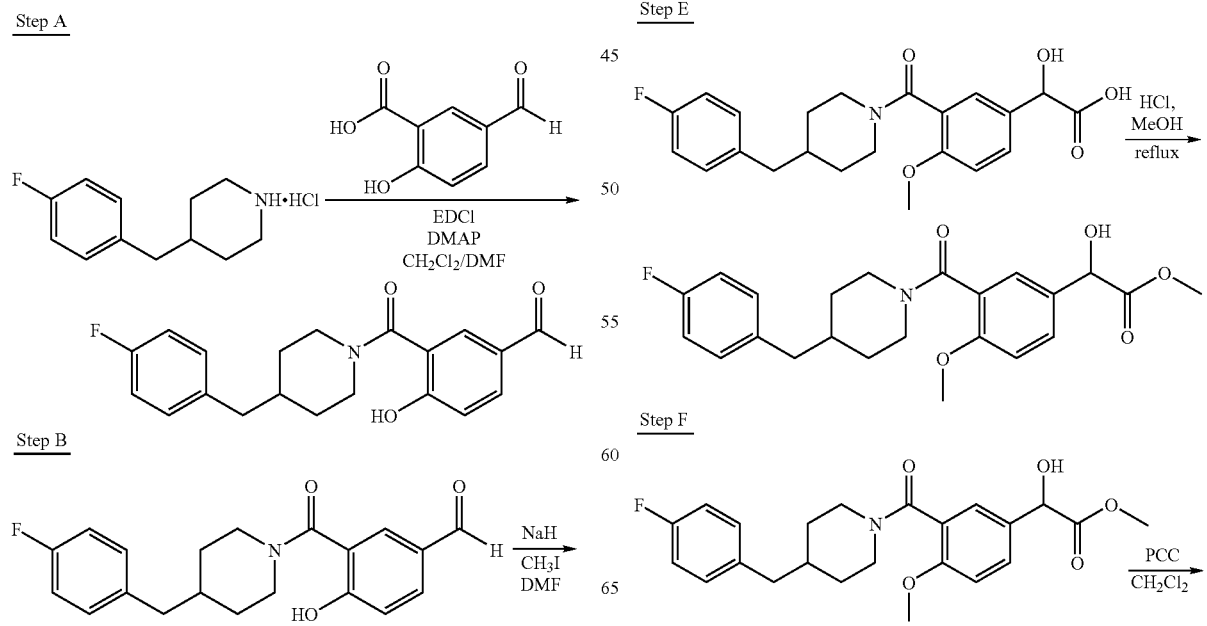

-continued
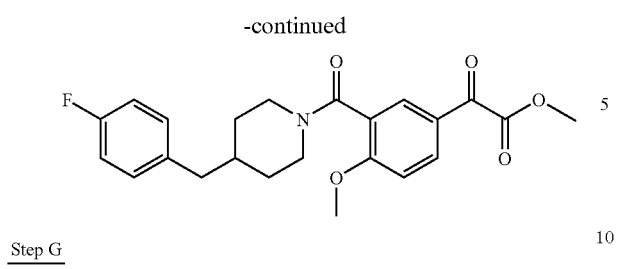
Step G
KOH, MeOH
reflux
Step H
a) SOCl₂
b) Dimethyl-amine
Scheme II
Step A
SOCl₂
MeOH
Step B
a) H₂O/HCl
b)
NaHCO₃
Dioxane
-continued
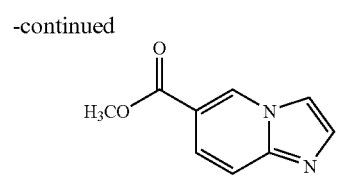
Step C
a) (COCl)₂
toluene
b) dimethyl-amine
Step D
NaOH
MeOH/H₂O
Step E
EDC

Scheme III
Step A
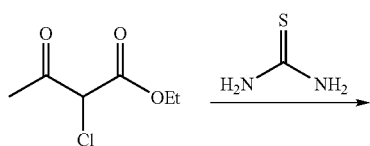
Step B
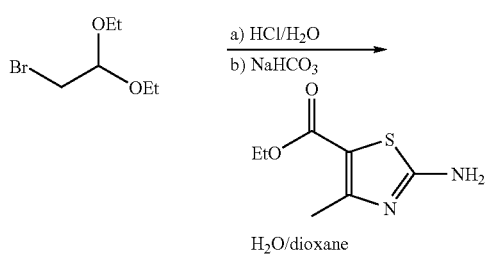
Step C
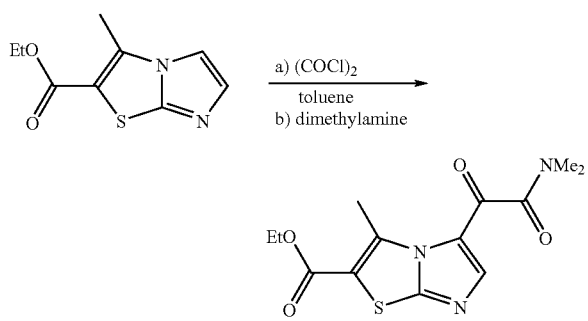
Step D
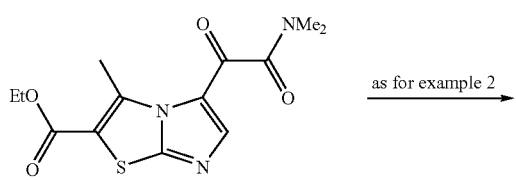
as for example 2
-continued
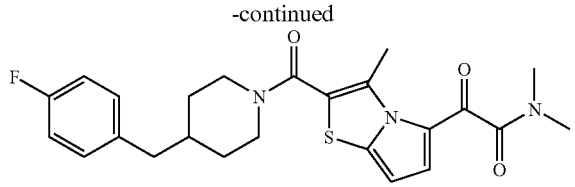
Scheme IV
Step A
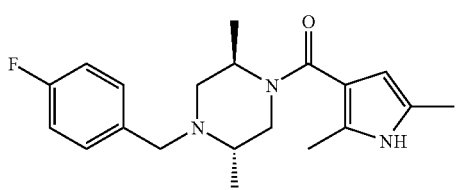
Step B
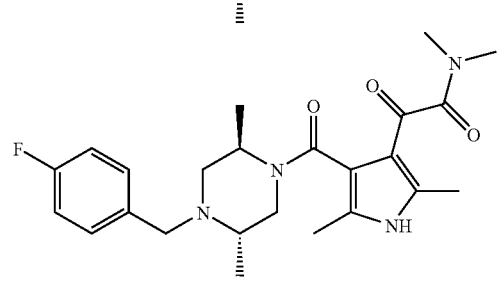
Scheme 4
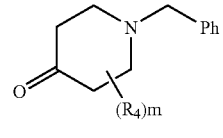
VIII
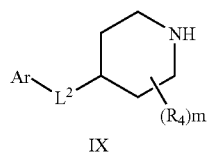
IX Assays for p38 α Kinase Inhibition For each of the assay procedures described below, the TNF-α production correlates to the activity of p38-α kinase.

A. Human Whole Blood Assay for p38 Kinase Inhibition

Venous blood is collected from healthy male volunteers into a heparinized syringe and is used within 2 hours of collection. Test compounds are dissolved in 100% DMSO and 1 µl aliquots of drug concentrations ranging from 0 to 1 mM are dispensed into quadruplicate wells of a 24-well microtiter plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% $CO_2$ at 37° C. Whole blood is cultured either undiluted or at a final dilution of 1:10 with RPMI 1640 (Gibco 31800+ $NaHCO_3$, Life Technologies, Rockville, Md. and Scios, Inc., Sunnyvale, Calif.). At the end of the incubation period, 10 µl of LPS (*E. Coli* 0111:B4, Sigma Chemical Co., St. Louis, Mo.) is added to each well to a final concentration of 1 or 0.1 µg/ml for undiluted or 1:10 diluted whole blood, respectively. The incubation is continued for an additional 2 hours. The reaction is stopped by placing the microtiter plates in an ice bath and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.).

$IC_{50}$ values are calculated using the concentration of inhibitor that causes a 50% decrease as compared to a control.

B. Enriched Mononuclear Cell Assay for p38 Kinase Inhibition

The enriched mononuclear cell assay, the protocol of which is set forth below, begins with cryopreserved Human Peripheral Blood Mononuclear Cells (HPBMCs) (Clonetics Corp.) that are rinsed and resuspended in a warm mixture of cell growth media. The resuspended cells are then counted and seeded at $1 \times 10^6$ cells/well in a 24-well microtitre plate. The plates are then placed in an incubator for an hour to allow the cells to settle in each well.

After the cells have settled, the media is aspirated and new media containing 100 ng/ml of the cytokine stimulatory factor Lipopolysaccharide (LPS) and a test chemical compound is added to each well of the microtiter plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

LPS Induced Cytokine Synthesis in HPBMCs

Cryopreserved HPBMC (cat#CC-2702 Clonetics Corp)
LGM-3 media (cat#CC-3212 Clonetics Corp)
LPS stock 10µg/ml (Cat. No. L 2630 serotype 0111:B4 Sigma)
Human TNF-α ELISA (R&D Systems)
DNase I (10 mg/ml stock)
Preparation of Cells
LGM-3 media warmed to 37° C.
5µl of DNase I stock added to 10 ml media.
Cells thawed rapidly and dispersed into above.
Centrifuge 200×g×10 min @ RT.
Pellet up in 10 ml sterile PBS.
Centrifuge 200×g×10 min @ RT.
Pellet resuspended in 10 ml LGM-3 then diluted to 50 ml with LGM-3.
Perform cell count.
Adjust to 1×E06 cells/well.
Seed 1 ml/well of a 24 well plate.
Place plate in incubator to plate down for 1 hour.
Preparation of Incubation Media
LGM-3 containing 100 ng/ml LPS (e.g. 50 ml media plus 0.5 ml LPS stock)
Aliquot into 2 ml aliquots and add 1000×inhibitor dilutions.
Incubation When cells have plated down aspirate media away and overlay with 1 ml relevant incubation media. Return plate to incubator for 2 hours or 24 hours. Remove supernatants after incubation to a labeled tube and either perform TNF (or other) ELISA immediately or freeze for later assay. $IC_{50}$ values are calculated using the concentration of inhibitor that causes a 50% decrease as compared to a control.

Administration and Use

The compounds of the invention are useful among other indications in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as Alzheimer's, coronary artery disease, congestive heart failure, cardiomyopathy, myocarditis, vasculitis, restenosis, such as occurs following coronary angioplasty, atherosclerosis, IBD, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, Gram-negative sepsis, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y., et al., *J Biol Chem* (1996) 271:17920–17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S., et al., *Biochem Biophys Res Comm* (1997) 235:533–538 and Stein, B., et al., *J Biol Chem* (1997) 272:19509–19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z., et al., *Biochem Biophys Res Comm* (1996) 228:334–340 and of p38-δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38-α and either the putative p38-β1 or p38-β2 or both were reported by Jiang, Kumar, and Stein cited above as well as by Eyers, P. A., et al., *Chem and Biol* (1995) 5:321–328. An additional paper by Wang, Y., et al., *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38-β activity results in hypertrophy, whereas activation of p38-α activity leads to myocyte apoptosis. Thus, selective inhibition of p38-α activity as compared to p38-β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention encompasses the use of compounds which selectively inhibit the activity of the p38-α isoform for treating conditions associated with activation of p38-α, in particular those associated with cardiac hypertrophy, ischemia or other environmental stress such as oxidation injury, hyperosmolarity or other agents or factors that activate p38-α kinase, or cardiac failure, for example, congestive heart failure, cardiomyopathy and myocarditis.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil; water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods. The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of p38 kinase can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implied above, although the compounds of the invention may be used in humans, they are also available for veterinary use in treating animal subjects.

The following examples are intended to illustrate but not to limit the invention. The compounds described and prepared in examples 1–4 below are inhibitors of p38-α kinase.

EXAMPLE 1

{3-[4-(4-Fluoro-benzyl)-piperidine-1-carbonyl]-4-methoxy-phenyl}-oxo-acetic acid methyl ester

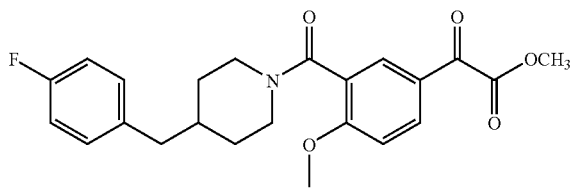

Step A

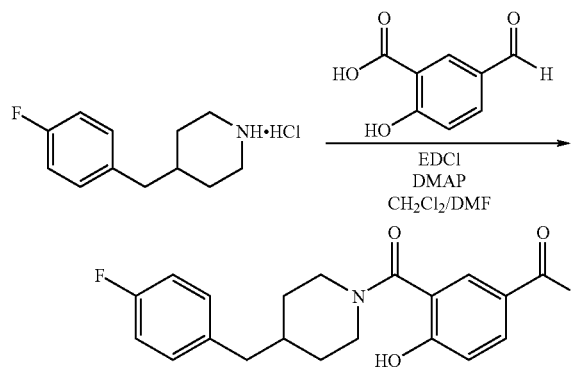

Under nitrogen protection, to a 250 mL R.B. dry flask containing 5.6 g (24.4 mMol) 4-fluoro-benzyl piperidine HCl salt was added 100 ml anhydrous CH$_2$Cl$_2$, followed by addition of 3.48 ml triethylamine (25 mMol). The suspension was allowed to stir at room temperature for a few minutes until it became a clear solution. To this solution was then added 4.37 g 5-formylsalicyclic acid (25 mMol), 4.8 g (25 mMol) of 1-ethyl-3-(3-dimethyl aminopropyl)-carbodiimide, 0.153 g (1.25 mMol) of 4-(dimethylamino)-pyridine. After overnight stirring, the reaction mixture was diluted with 100 mL of CH$_2$Cl$_2$, washed with H$_2$O, brine. The organic layers were then dried over anhydrous sodium sulfate, concentrated and purified by column chromatogra phy eluting with CH$_2$Cl$_2$, giving 3.65 g (10.7 mMol) of desired product. (yield: 43.8%)

Step B

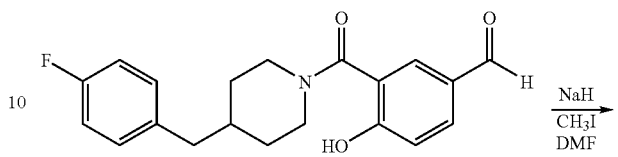

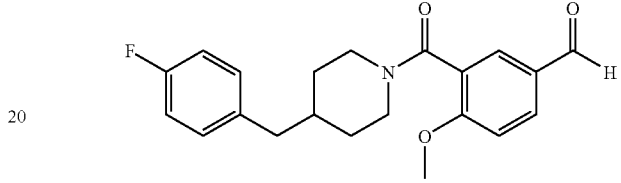

3.62 gram (10.6 mMol) aldehyde was dissolved in 100 mL anhydrous DMF under an argon atmosphere. To this solution, at 0° C. was added 4.66 g NaH (60% dispersion in mineral oil, 11.7 mMol). The reaction was allowed to stir at 0° C. for 0.5 h before warming up to room temperature, stirring continued until there were no more bubbles produced. The flask was then cooled to 0° C. again, followed by addition of 0.73 mL of methyl iodide (11.7 mMol). After stirring at 0° C. for 0.5 h, the reaction was warmed up to room temperature, and continued stirring for another 4 h. DMF was evaporated off under reduced pressure. The resulting residue was re-dissolved in 100 mL of CH$_2$Cl$_2$, washed twice with H$_2$O, and brine. Organic layers were dried over anhydrous sodium sulfate, concentrated and purified by column chromatography in a gradient of 100% CH$_2$Cl$_2$ to 2% MeOH/CH$_2$Cl$_2$. 2.65 g (7.46 mMol) of product was obtained in a yield of 70.4%.

Step C

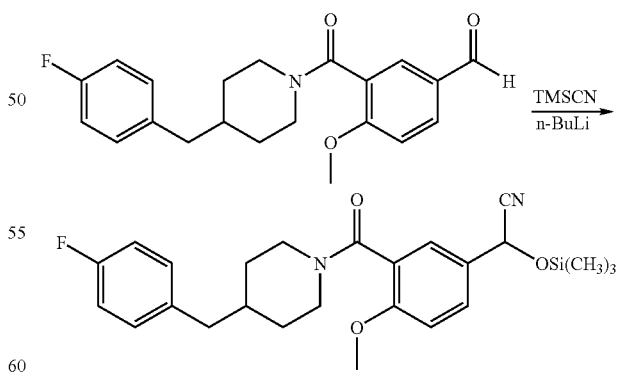

Under nitrogen protection, 2.64 g (7.43 mMol) of aldehyde was dissolved in 75 mL anhydrous THF. At 0° C., to this solution was added 1.1 mL of trimethylsilyl cyanide (8.2 mMol), followed by addition of 2–3 drops of n-butyllithium (2.5 M solution in hexane). Stirring at 0° C. was continued for 2 h before warmed up to room temperature and stirred overnight. After removing solvents by rotary evaporation, product was obtained in almost quantitative yield as a white power. Without further purification, the material was used directly in next step.

Step D

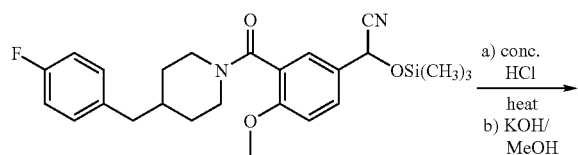

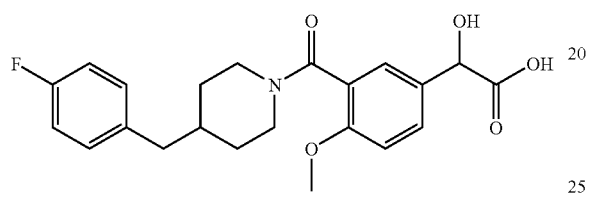

The material obtained from last step was diluted with 60 mL of concentrated HCl and heated to 80° C. with an oil bath overnight. After overnight heating, the aqueous solution was diluted with 100 mL H$_2$O and aqueous solution was extracted with CH$_2$Cl$_2$ (100 mL×3). Organic layers were washed with brine, dried over sodium sulfate, and concentrated. The residue was then re-dissolved in about 70 mL MeOH, followed by addition of 1.7 g (30.3 mMol) of KOH and the solution was warmed to reflux for 2 h. Reaction was then cooled to room temperature, concentrated, and dried under vacuum. Several grams of crushed ice was added into the flask and acidified with 10% aqueous HCl. Water (60 mL) was added to dilute the solution, and this aqueous solution was extracted with CH$_2$Cl$_2$ (100 mL×3). Organic layers were washed with brine, dried over sodium sulfate, concentrated to give 2.5 g (6.23 mMol) of product.

Step E

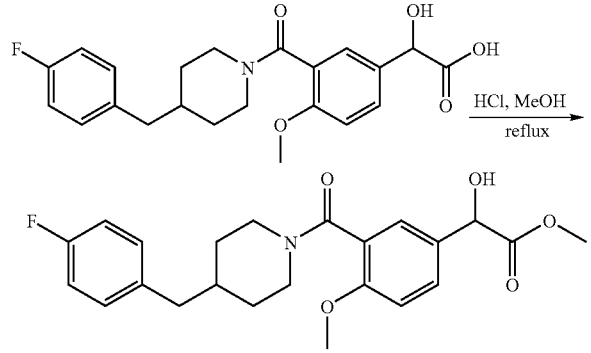

In a 50 mL R.B. flask containing a condenser, 130 mg of α-hydroxy acid was dissolved in 4 ml of concentrated HCl:MeOH (1:9) and warmed to reflux. After 1 h, the reaction was cooled to RT and concentrated under reduced pressure. Resulting residue was re-dissolved in 20 mL ethyl acetate and the ethyl acetate layer was washed with 20 mL H$_2$O, twice with 20 ml saturated NaHCO$_3$ solution, and brine. Organic layer was dried over anhydrous sodium sulfate and concentrated to give 141 mg of crude product.

Step F

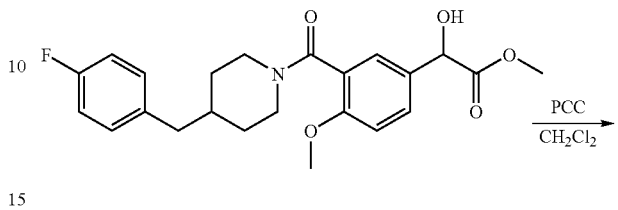

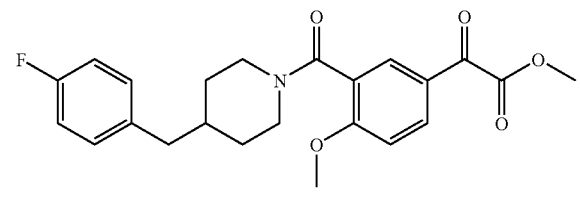

123 mg of methyl ester was dissolved in 4 ml CH$_2$Cl$_2$ followed by addition of excess of pyridinium chlorate (1 g, 20 wt. % on basic alumina). The resulting suspension was stirred at room temperature over 24 hours. Solid was filtered and washed with CH$_2$Cl$_2$. Combined organic solution was concentrated and product was purified by Preparative thin-layer chromatography with 1% MeOH/CH$_2$Cl$_2$ as eluting solution, to give 26 mg of desired product.

EXAMPLE 2

2-{2-[4-(4-Fluoro-benzyl)-piperidine-1-carbonyl]-3-methyl-imidazo[2,1-b]thiazol-5-yl}-N,N-dimethyl-2-oxo-acetamide

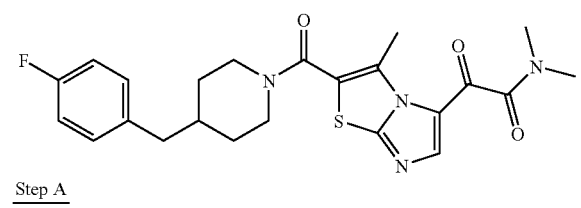

Step A

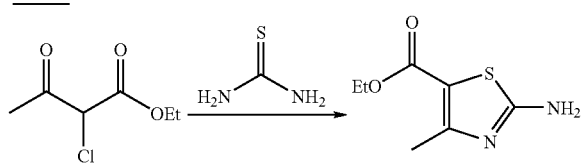

Thiourea (3.81 g) and ethyl 2-chloroacetoacetate (8.23 g) were combined in EtOH (100 mL) and heated at reflux for 14 h. After cooling to RT the EtOH was removed in vacuo and the crude product dissolved in H$_2$O and neutralized with NaHCO$_3$ followed by extraction with ethyl acetate. The combined extracts were dried, filtered, and concentrated to yield the product as a white powder (8.69 g).

Step B

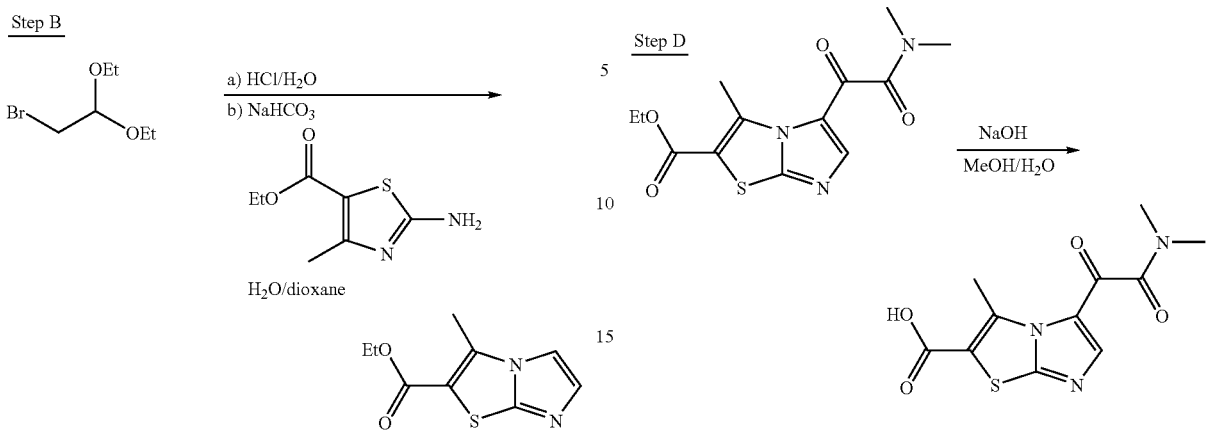

To bromoacetaldehyde diethylacetal (11.2 mMol, 2.20 g) in H₂O (75 mL) was added concentrated HCl (1.15 mL) dropwise. After stirring at RT for 14 h the mixture was heated at 80° C. for 30 min. After cooling to RT NaHCO₃ (14.5 mMol, 1.22 g) was cautiously added and stirring was continued for 2 h. The ester (8.9 mMol, 1.66 g) was then added and the mix was stirred an additional 1 h before adding dioxane (50 mL). After 30 min the mix was heated to 100 ° C. for 48 h. After cooling to RT the dioxane was removed by rotary evaporation. The aqueous layer was extracted with CH₂Cl₂. The combined organics were dried (Na₂SO₄), filtered and concentrated. Radial chromatography (10% MeOH in CH₂Cl₂) yielded 122 mg of the desired product.

Step C

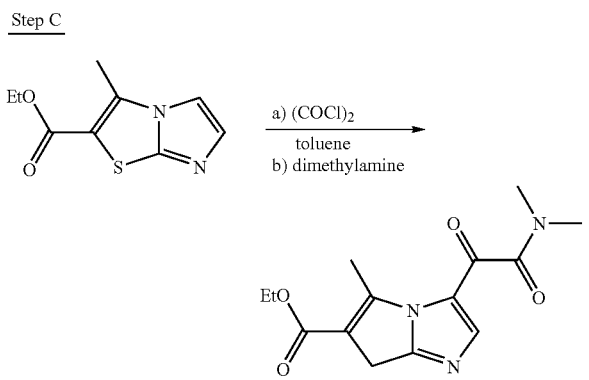

To the ester (0.19 mMol, 40 mg) in toluene (0.76 mL) at RT was added a 2.0 M solution of oxalyl chloride in CH₂Cl₂ (0.285 mL). The reaction vessel was placed under N₂, sealed, and placed at 125° C. for 12 h. After cooling to RT the volatiles were removed under vacuum. To the crude acid chloride was added CH₂Cl₂ (0.76 mL) and after cooling to 0° C. a 2.0 M solution of dimethylamine in THF (0.285 mL) was added dropwise. The reaction mixture was stirred an additional 30 min at 0° C. and then warmed to RT. After 30 min the reaction was quenched with H₂O and extracted with CH₂Cl₂. The combined extracts were washed with brine and then dried (Na₂SO₄), filtered and concentrated. After radial chromatography (10% MeOH in CH₂Cl₂) 38 mg of the product was obtained.

Step D

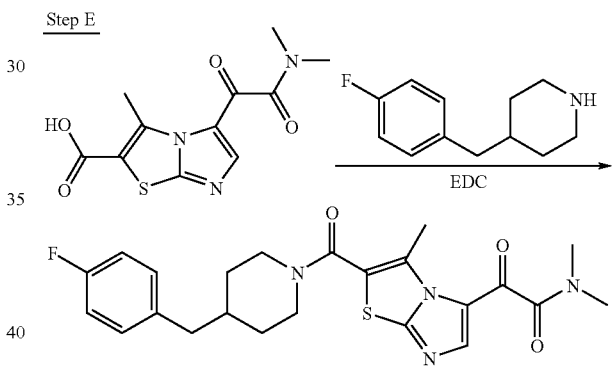

To the ester (0.12 mMol, 38 mg) in MeOH (0.25 mL) and H₂O (0.25 mL) was added NaOH (0.985 N in H₂O, 122 µL). The mixture was stirred at RT for 14 h at which time it was acidified with aq. HCl and extracted with ethyl acetate. The combined extracts were dried (Na₂SO₄), filtered, and concentrated to yield 19 mg of the product which carried on to the next step without purification.

Step E

To the acid (0.14 mMol, 19 mg) in CH₂Cl₂ (0.56 mL) was added 4-fluorobenzylpiperidine (0.17 mMol, 39 mg) followed by EDC (0.17 mMol, 33 mg) and DMAP (4 mg). The mix was stirred at RT for 14 h before quenching with H₂O and extracting with CH₂Cl₂. The combined extracts were dried (Na₂SO₄), filtered, and concentrated. After radial chromatography 20 mg of the desired compound was obtained.

EXAMPLE 3

2-{6-[4-(4-Fluoro-benzyl)-piperidine-1-carbonyl]-imidazo[1,2-a]pyridin-3-yl}-N,N-dimethyl-2-oxo-acetamide

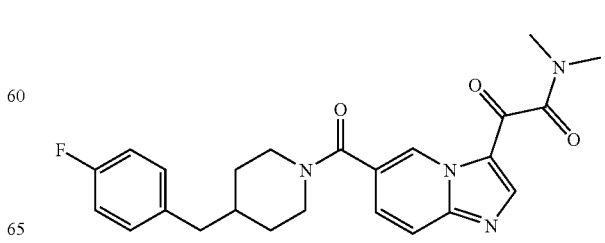

Step A

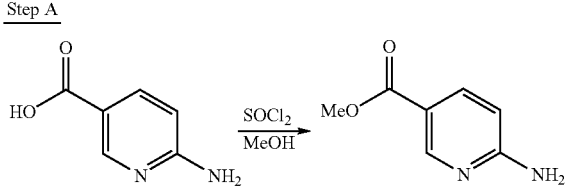

To 6-aminonicotinic acid (75 mMol, 10.36 g) in MeOH (300 mL) at −78° C. was added SOCl₂ (187.5 mMol, 22.31 g, 13.7 mL) dropwise over 30 min. The mixture was then allowed to RT. The mix was then refluxed for 12 h at which time it was cooled and the volatiles removed using rotary evaporation. The resulting white solid was dissolved in H₂O, neutralized with NaHCO₃, and extracted with ethyl acetate. The combined organics were dried (Na₂SO₄), filtered, and concentrated to yield 10.06 g of a white powder.

Step B

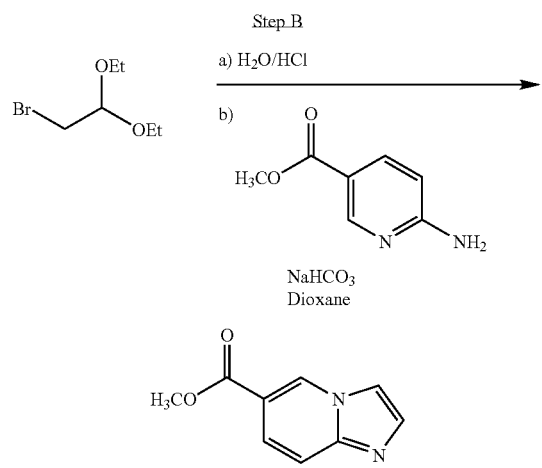

To bromoacetaldehyde diethylacetal (44.6 mMol, 8.79 g) in H₂O (300 mL) was added concentrated HCl (4.6 mL) dropwise. After stirring at RT for 14 h the mixture was heated at 80° C. for 30 min. After cooling to RT, NaHCO₃ (58.7 mMol, 4.88 g) was cautiously added and stirring was continued for 2 h. The ester (35.6 mMol, 5.41 g) was then added and the mix was stirred an additional 1 h before adding dioxane (200 mL). After 30 min the mix was heated to 100° C. for 48 h. After cooling to RT the dioxane was removed by rotary evaporation. The aqueous layer was extracted with CH₂Cl₂. The combined organics were dried (Na₂SO₄), filtered and concentrated to yield a yellow paste (217 mg) which was carried on to the next step without further purification.

Step C

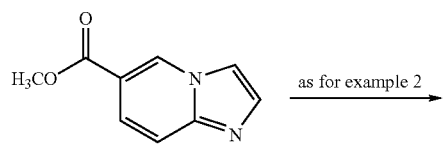

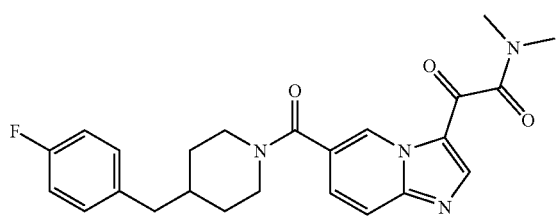

Synthesis of 2-{6-[4-(4-fluoro-benzyl)-piperidine-1-carbonyl]-imidazo[1,2-a]pyridin-3-yl}-N,N-dimethyl-2-oxo-acetamide was carried out through the same series of steps as for 2-{2-[4-(4-Fluoro-benzyl)-piperidine-1-carbonyl]-3-methyl-imidazo[2,1-b]thiazol-5-yl}-N,N-dimethyl-2-oxo-acetamide.

EXAMPLE 4

2-{4-[4-(4-Fluoro-benzyl)-2,5-trans-dimethyl-piperazine-1-carbonyl]-2,5-dimethyl-1H-pyrrol-3-yl}-N,N-dimethyl-2-oxo-acetamide

Step A

To 2,5-Dimethyl-1H-pyrrole-3-carboxylic acid (1.09 g) and 1-(4-Fluoro-benzyl)-trans-2,5-dimethyl-piperazine (1.59 g) in CH₂Cl₂ was added EDCI (1.51 g) and catalytic DMAP. The reaction mixture was stirred at RT for 12 h at which time it H₂O was added. The mix was extracted with CH₂Cl₂. The combined extracts were dried, filtered, and concentrated. After column chromatography (silica gel, (1:2) ethyl acetate/hexane to (7:3) ethyl acetate/hexane) 540 mg of the desired product was obtained.

Step B

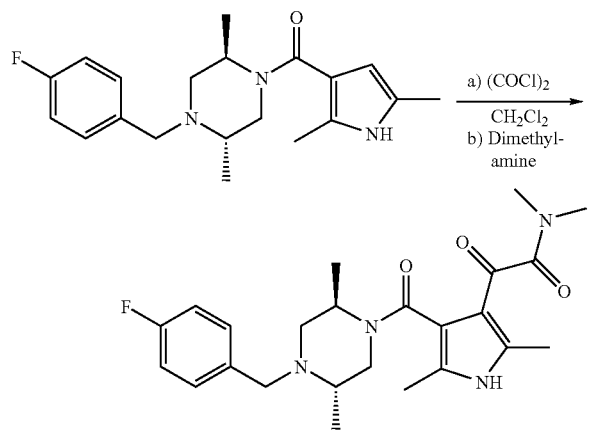

A solution of (2,5-dimethyl-1H-pyrrol-3-yl)-[4-(4-fluoro-benzyl)-trans-2,5-dimethyl-piperazine-1-yl]-methanone (340 mg) in $CH_2Cl_2$ (25 mL) was cooled to 0° C. and a solution of oxalyl chloride (2.0 M in $CH_2Cl_2$, 2.0 mL) was added. Stirring was continued for 1 h at 0° C. and then the mix was allowed to warm to RT and stir for 1 h. The solvent was removed in vacuo and then replaced with $CH_2Cl_2$ (25 mL). After cooling to 0° C. dimethylamine (2.0 M solution in THF, 4.0 mL) was added dropwise. Stirring was continued for 30 min at which time it was warmed to RT. After 30 min the reaction was quenched with $H_2O$ and extracted with $CH_2Cl_2$. The combined extracts were dried, filtered, and concentrated to yield the desired product which was purified by silica gel column chromatography ((1:1) ethyl acetate/hexane to ethyl acetate followed by (95:5) ethyl acetate/methanol to (90:10) ethyl acetate/methanol) to yield 60 mg of the product.

ADDITIONAL EXAMPLES

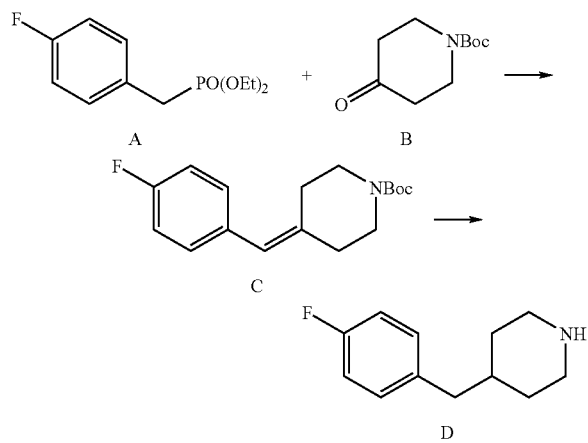

Synthesis of D

STEP 1: The phosphonate A (38.4 g) and the piperidone B (35.4) were dissolved in anhydrous dimethylformamide (400 mL). To this sodium hydride (60% suspension in oil) was added in portions while the reaction is maintained at 0° C. After the addition of sodium hyride was complete the reaction mixture was stirred for 30 min. and then the ice bath was removed, the reaction was allowed to stir for 6 h as it slowly warmed to ambient temperature. The reaction was again cooled in an ice bath and quenched with methanol. Water was added to the reaction mixture, and the product extracted with ethyl acetate. The ethyl acetate layer was washed with saturated sodium chloride and dried over anhydrous magnesium sulfate. The solvent was removed to gives the crude alkene, which is purified by column chromatography eluting with ethyl acetate/hexane (1:9) to give 21.8 g of the desired product C.

STEP 2: 10 .1 g of C was dissolved in 50 mL methanol. After purging the solution with nitrogen, 5% Palladium on carbon (1 g) catalyst was added followed by 1 mL acetic acid. The parr container containing the reaction mixture was hydrogenated for 4 h at 40–50 psi. The reaction mixture was filtered through celite and concentrated. The residue was treated with 2 M hydrochloric acid in ether to convert to the hydrochloric acid salt. The white solid that was obtained was dried under vacuum, extensively, to give 7.8 g of D as the hydrochloric acid salt.

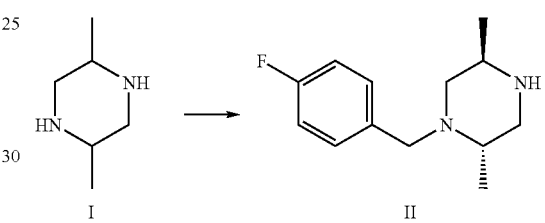

Synthesis of II:

STEP 1: To a solution of dimethyl piperazine I (25 g) in 300 ml of absolute ethanol was added 400 ml of 2 N hydrogen chloride in diethyl ether. The solution was warmed to 70° C. in an oil bath for 20 minutes. The solution was then cooled to room temperature and set at 6° C. overnight. The solid obtained, was collected by filtration. Yield 39.8 g (dihydrochloride salt of trans-2,5 dimethylpiperazine) after drying overnight under high vacuum.

STEP 2: An ethanol solution of 42.9 g of dimethyl piperazine dihydrochloride from STEP 1 and 26.1 g trans-2,5 dimethylpiperazine was vigorously stirred in an oil bath at 80° C. until all starting materials were dissolved. The temperature of oil bath was reduced to 65° C. and 33.1 g of 4-fluro benzylchloride was added. After stirring at this temperature for 30 min., the solution was placed in a 6° C. refrigerator overnight. The solid was removed from the solution by filtration and excess of 2 N hydrogen chloride in diethyl ether was added to the filtrate. The filtrate was kept at 6° C. overnight and the solid collected. The solid was suspended in 5% sodium hydroxide aqueous solution and extracted three times with ethyl acetate. The organic layer was dried over sodium sulfate and dried down to give a yellow oil.

STEP 3: A solution of 50.7 g (L)-tartaric acid in 130 ml of boiling methanol was added to 70 ml of hot methanol solution of 37.5 g of the product from STEP 2. The solution was set at 6° C. for 96 hours before collection of white fine crystals by filtration. This material was recrystallized from boiling methanol. The product was collected by filtration after being kept at a 6° C. overnight. Yield 30.5 g of ditartaric acid salt ([α]=+43.2°, c=1).

What is claimed is:

1. A compound of the formula:

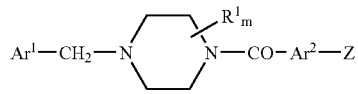

or the pharmaceutically acceptable salts thereof, or a pharmaceutical composition thereof, wherein:

$Ar^1$ is an aryl group substituted with 0–5 non-interfering substituents selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl or heteroaryl, and wherein two of said optional substituents on adjacent positions can be joined to form a fused, optionally substituted aromatic or nonaromatic, saturated or unsaturated ring which contains 3–8 members;

each $R^1$ is independently a noninterfering substituent selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl or heteroaryl and two of $R^1$ on adjacent positions can be joined to form a fused, optionally substituted aromatic or nonaromatic, saturated or unsaturated ring which contains 3–8 members, or $R^1$ is =O or an oxime, oximeether, oximeester or ketal thereof;

m is 0–4;

$Ar^2$ is

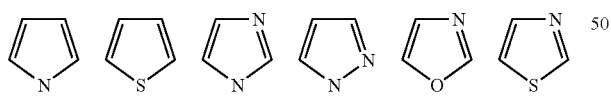

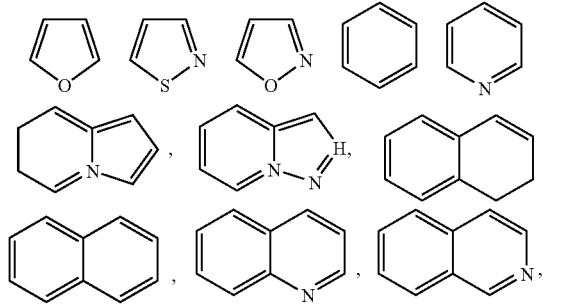

each optionally substituted by one or more R";

wherein each R" is independently selected from the group consisting of H, alkyl, acyl, aryl, arylalkyl, heteroalkyl, heteroaryl, halo, OR, $NR_2$, SR, NRCOR, alkyl-OOR, RCO, COOR, and CN, wherein each R is independently H, alkyl, aryl, heteroalkyl, or heteroaryl where two adjacent R" groups may form a fused ring;

wherein H shown as a ring member is N or CR' wherein R' is hydrogen or (a) alkyl, alkenyl, alkynyl, aryl, arylalkyl, acyl, aroyl, heteroaryl, heteroalkyl, heteroalkenyl, heteroalkynyl, heteroalkylaryl, NH-aroyl or halo; or (b) OR, $NR_2$, SR, SOR, $SO_2R$, OCOR, NRCOR, $NRCONR_2$, NRCOOR, $OCONR_2$, RCO, COOR, alkyl-OOCR, $SO_3R$, $CONR_2$, $SO_2NR_2$, $NRSO_2NR_2$, CN, $CF_3$, $R_3Si$, and $NO_2$, wherein each R is independently H, alkyl, alkenyl, aryl, heteroalkyl, heteroalkenyl or heteroaryl;

Z is $-W_i\text{-}COX_jY$ wherein Y is $COR^3$ or tetrazole; 1,2,3-triazole; 1,2,4-triazole; or imidazole; $R^3$ is H or a noninterfering substituent which is straight or branched chain alkyl, alkenyl, alkynyl, aryl, arylalkyl, heteroalkyl, heteroaryl, or heteroarylalkyl, each optionally substituted with halo, alkyl, heteroalkyl, SR, SOR, $SO_2R$, $SO_2NR_2$, OR, $NR_2$, OCOR, NRCOR, $NRCONR_2$, $NRSO_2R$, $NRSO_2NR_2$, $OCONR_2$, CN, COOR, $CONR_2$, COR, or $R_3Si$ wherein each R is independently H, alkyl, alkenyl, aryl, heteroalkyl, heteroalkenyl or heteroaryl, or wherein $R^3$ is OR, $NR_2$, SR, $NRCONR_2$, $OCONR_2$, or $NRSO_2NR_2$, wherein each R is independently H, alkyl, alkenyl, aryl, heteroalkyl, heteroalkenyl or heteroaryl, and wherein two R attached to the same atom may form a 3–8 member carbocyclic or heterocyclic ring and wherein said ring may further be substituted by alkyl, alkenyl, alkynyl, aryl, arylalkyl, heteroalkyl, heteroaryl, heteroarylalkyl, each optionally substituted with halo, SR, OR, $NR_2$, OCOR, NRCOR, $NRCONR_2$, $NRSO_2R$, $NRSO_2NR_2$, $OCONR_2$, or $R_3Si$ wherein each R is independently H, alkyl, alkenyl, aryl, heteroalkyl, heteroalkenyl or heteroaryl wherein two R attached to the same atom may form a 3–8 member ring, optionally substituted as above defined, each of W and X is an alkylene of 2–6 Å, and each of i and j is independently 0 or 1.

2. The compound of claim 1 wherein each of i and j is 0.

3. The compound of claim 1 wherein the portion of said compound represented by Ar²—Z is selected from the following:

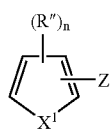
(I)

wherein n is 0, 1 or 2; X¹ is NR''; and each R'' is independently selected from the group consisting of H, alkyl, acyl, aryl, arylalkyl, heteroalkyl, heteroaryl, halo, OR, NR₂, SR, NRCOR, alkyl-OOCR, RCO, COOR, and CN, wherein each R is independently H, alkyl, aryl, heteroalkyl, or heteroaryl; and two adjacent R'' groups may form a fused ring;

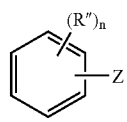
(II)

wherein n is 0–4; each R'' is independently selected from the group consisting of H, alkyl, acyl, aryl, arylalkyl, heteroalkyl, heteroaryl, halo, OR, NR₂, SR, NRCOR, alkyl-OOCR, RCO, COOR, and CN, wherein each R is independently H, alkyl, aryl, heteroalkyl, or heteroaryl where two adjacent R'' groups may form a fused ring; and one or more ring carbons may be optionally replaced with nitrogen;

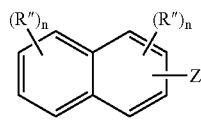
(III)

wherein each n is independently 0 to 3; each R'' is independently selected from the group consisting of H, alkyl, acyl, aryl, arylalkyl, heteroalkyl, heteroaryl, halo, OR, NR₂, SR, NRCOR, alkyl-OOCR, RCO, COOR, and CN, wherein each R is independently H, alkyl, aryl, heteroalkyl, or heteroaryl, where two adjacent R'' groups may form a fused ring; and one or more ring carbons may be optionally replaced with nitrogen;

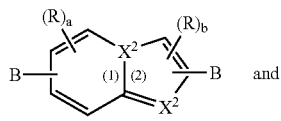
(IV-a)

and

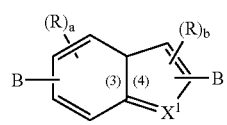
(IV-b)

wherein one B is absent and the other is Z; wherein a is 0 to 3; b is 0–1; each R'' is independently selected from the group consisting of H, alkyl, acyl, aryl, arylalkyl, heteroalkyl, heteroaryl, halo, OR, NR₂, SR, NRCOR, alkyl-OOCR, RCO, COOR, and CN, wherein each R is independently H, alkyl, aryl, heteroalkyl, or heteroaryl where two adjacent R'' groups may form a fused ring.

4. The compound of claim 3 wherein Ar²—Z is:

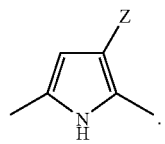

5. The compound of claim 4 where the compound is:

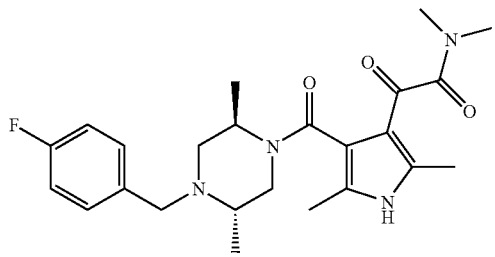

6. The compound of claim 3 wherein Ar²—Z is:

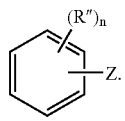

7. The compound of claim 6 wherein each R'' is methoxy.

8. The compound of claim 7 wherein n is 1.

9. The compound of claim 3 wherein Ar²—Z is structure (III).

10. The compound of claim 3 wherein Ar²—Z is structure (IV-a) or (IV-b).

11. The compound of claim 10 wherein Ar²—Z is (IV-b).

12. The compound of claim 11 wherein Ar²—Z is:

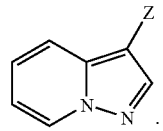

13. The compound of claim 1 wherein Ar¹ is optionally substituted phenyl.

14. The compound of claim 13 wherein said optional substitution is by halo, OR, or alkyl.

15. The compound of claim 14 wherein said phenyl is unsubstituted or has a single substituent.

16. The compound of claim 1 wherein each R¹ is halo, OR, or alkyl.

17. The compound of claim 16 wherein m is 0, 1, or 2.

18. The compound of claim 17 wherein m is 2 and both R¹ are alkyl.

19. A pharmaceutical composition for treating conditions characterized by enhanced p38-α activity which composition comprises a therapeutically effective amount of a compound of claim 1 along with a pharmaceutically acceptable excipient.

20. A method to treat a condition mediated by p38-α kinase comprising administering to a subject in need of such treatment a compound of claim 1 or a pharmaceutical composition thereof, wherein said condition is multiple sclerosis, IBD, rheumatoid arthritis, rheumatoid spondylitis, osteoarthritis, gouty arthritis, sepsis, endotoxic shock, asthma, adult respiratory distress syndrome, reperfusion injury, psoriasis, cerebral malaria, chronic pulmonary inflammatory disease, silicosis, pulmonary sarcosis, a bone resorption disease, graft-versus-host reaction, Crohn's Disease, ulcerative colitis, or pyresis.

* * * * *